US00PP23714P3

(12) United States Plant Patent
Bak et al.

(10) Patent No.: US PP23,714 P3
(45) Date of Patent: Jul. 2, 2013

(54) ***GUZMANIA* HYBRID NAMED 'JUNO'**

(50) Latin Name: ***Guzmania* sp.**
Varietal Denomination: JUNO

(75) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 37 days.

(21) Appl. No.: 13/137,067

(22) Filed: Jul. 19, 2011

(65) Prior Publication Data

US 2013/0025013 P1 Jan. 24, 2013

(51) Int. Cl.
*A01H 5/00* (2006.01)

(52) U.S. Cl.
USPC ..... Plt./371

(58) Field of Classification Search
USPC ..... Plt./371
See application file for complete search history.

(56) References Cited

PUBLICATIONS

Application information from Community Plant Variety Office (CPVO) website for corresponding CPVO application No. 2011/1055 filed Apr. 26, 2011 (1 page). (http://www.cpvoextranet.cpvo.europa.eu).

Application information from Agricultural Production Bureau, Ministry of Agriculture, Forestry and Fisheries website for corresponding Japanese Plant Breeders' Rights application No. 25970 filed May 30, 2011 (1 page). (http://www.hinsyu.maff.go.jp/vips2/cmm/apCMM110.aspx?Moss=1).

*Primary Examiner* — Susan McCormick Ewoldt
(74) *Attorney, Agent, or Firm* — Foley & Lardner LLP

(57) ABSTRACT

A new and distinct *Guzmania* plant named 'JUNO' characterized by solid growth habit; funnel-form rosette plant, measuring about 57 cm in height (above the pot when flowering); numerous, green color foliage, measuring about 45 cm in length and about 3.0 cm to 3.5 cm in width; superior floral bract production; bracts have a unique pinkish-red inflorescence (RHS 47A); compound inflorescence, measuring from about 17 cm in height and about 18 cm in diameter; and long-lasting habit.

2 Drawing Sheets

Latin name of the genus and species of the claimed plant: *Guzmania* sp.

Variety denomination: 'JUNO'.

BACKGROUND OF THE INVENTION

The present invention relates to a new and distinct hybrid cultivar of *Guzmania* plant, botanically known as *Guzmania* sp., of the family Bromeliaceae, and hereinafter referred to as 'JUNO'.

*Guzmania* is native to tropical America. *Guzmania* is predominantly epiphytic with a few terrestrial species and is native to the tropics. For the most part, species vary in diameter from 7 or 8 inches to 3 or 4 feet and have rosettes of glossy, smooth-edged leaves. Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived. *Guzmania* may be advantageously grown as pot plants for greenhouse or home use. Typically, the plants are shaded from direct sunlight. During the spring to autumn period, the central vase-like part of the leaf rosette is normally filled with water.

The new *Guzmania* 'JUNO' was discovered and selected by the inventors in 2002 as a single flowering plant in a controlled breeding program in Assendelft, The Netherlands. The new *Guzmania* 'JUNO' originated from a naturally occurring whole plant mutation of *Guzmania* (hybrid) 'LUNA' (unpatented).

Asexual reproduction of the new *Guzmania* cultivar was first performed by off-shoots beginning in 2003 and then by tissue culture beginning in 2005 in Assendelft, The Netherlands, with first flowering after asexual reproduction occurring in 2009 in Assendelft, The Netherlands. Asexual reproduction of the *Guzmania* 'JUNO' has demonstrated that the combination of characteristics as herein disclosed for the new cultivar are firmly fixed arid retained through successive generations of asexual reproduction. The new cultivar reproduces true to type.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

BRIEF SUMMARY OF THE INVENTION

The following traits have been repeatedly observed and are determined to be unique characteristics of 'JUNO' which in combination distinguish this *Guzmania* as a new and distinct cultivar:

1. Solid growth habit;
2. Funnel-form rosette plant, measuring about 57 cm in height (above the pot when flowering);
3. Numerous, green color foliage, measuring about 45 cm in length and about 3.0 cm to 3.5 cm in width;
4. Superior floral bract production;

5. Bracts have a unique pinkish red inflorescence (RHS 47A);
6. Compound inflorescence, measuring from about 17 cm in height and about 18 cm in diameter; and
7. Long-lasting habit.

When the new *Guzmania* 'JUNO' is compared to the parent variety, the *Guzmania* hybrid 'LUNA' (unpatented), plants of the new *Guzmania* 'JUNO' differ from plants of 'LUNA' primarily in the following characteristics:

Plants of 'JUNO' produce compound inflorescence which are pinkish red (closest to RHS 47A) in color, whereas plants of 'LUNA' produce compound inflorescence which are purple (closest to RHS 59A) in color.

Of the many commercial cultivars known to the present inventors, the most similar in comparison to the new *Guzmania* 'JUNO' is the *Guzmania* hybrid 'FREYA' (patented, U.S. Plant Pat. No. 21,461). Plants of the new *Guzmania* 'JUNO' differ from plants of 'FREYA' primarily in the following characteristics:

Plants of 'JUNO' produce compound inflorescence which are pinkish red (closest to RHS 47A) in color, whereas plants of 'FREYA' produce compound inflorescence which are red-purple (closest to RHS 61B) in color.

BRIEF DESCRIPTION OF THE PHOTOGRAPHS

The accompanying photographs illustrate the overall appearance of the new *Guzmania* 'JUNO' showing the colors as true as is reasonably possible with colored reproductions or this type. Colors in the photographs may differ slightly from the color values cited in the detailed botanical description which accurately describes the color of 'JUNO'.

DETAILED BOTANICAL DESCRIPTION

Figure 1:
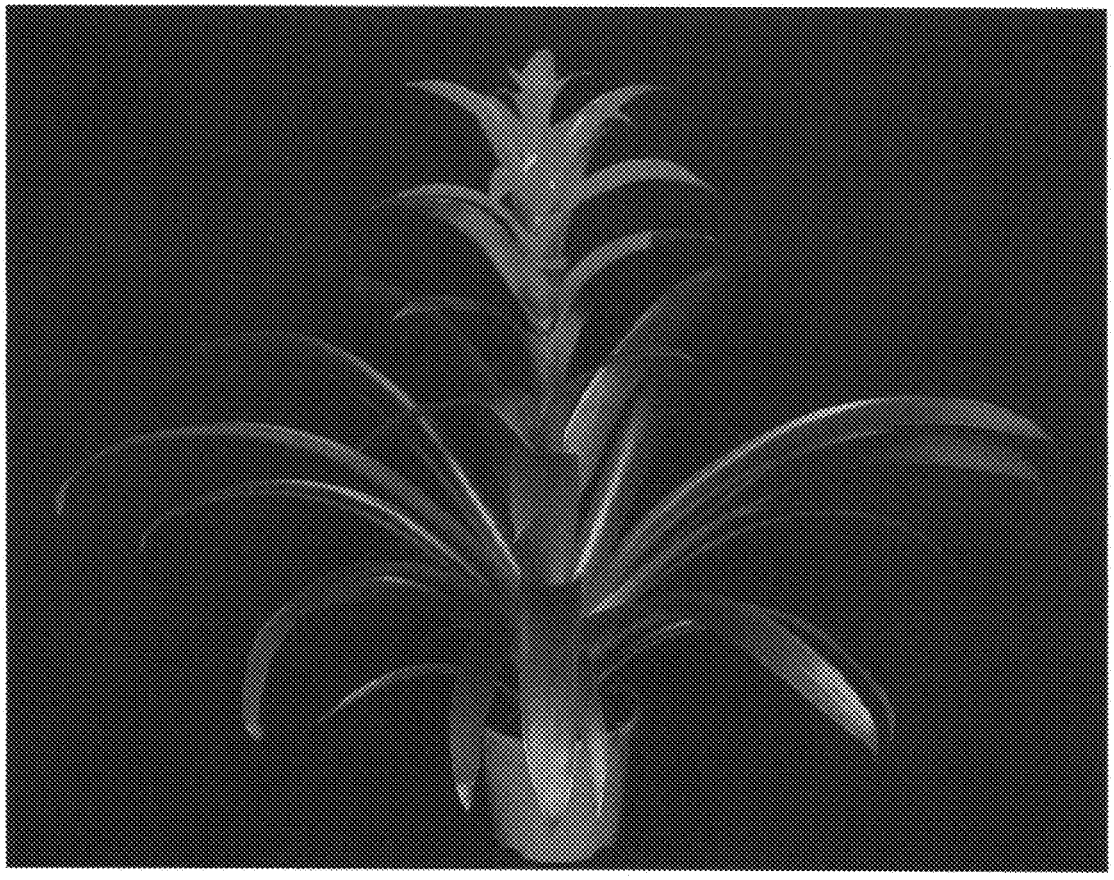
FIG. 1 shows a side view perspective of the primary and top bracts produced by a typical-potted, flowering plant of 'JUNO', at 12 months of age from potting size.
Figure 2:
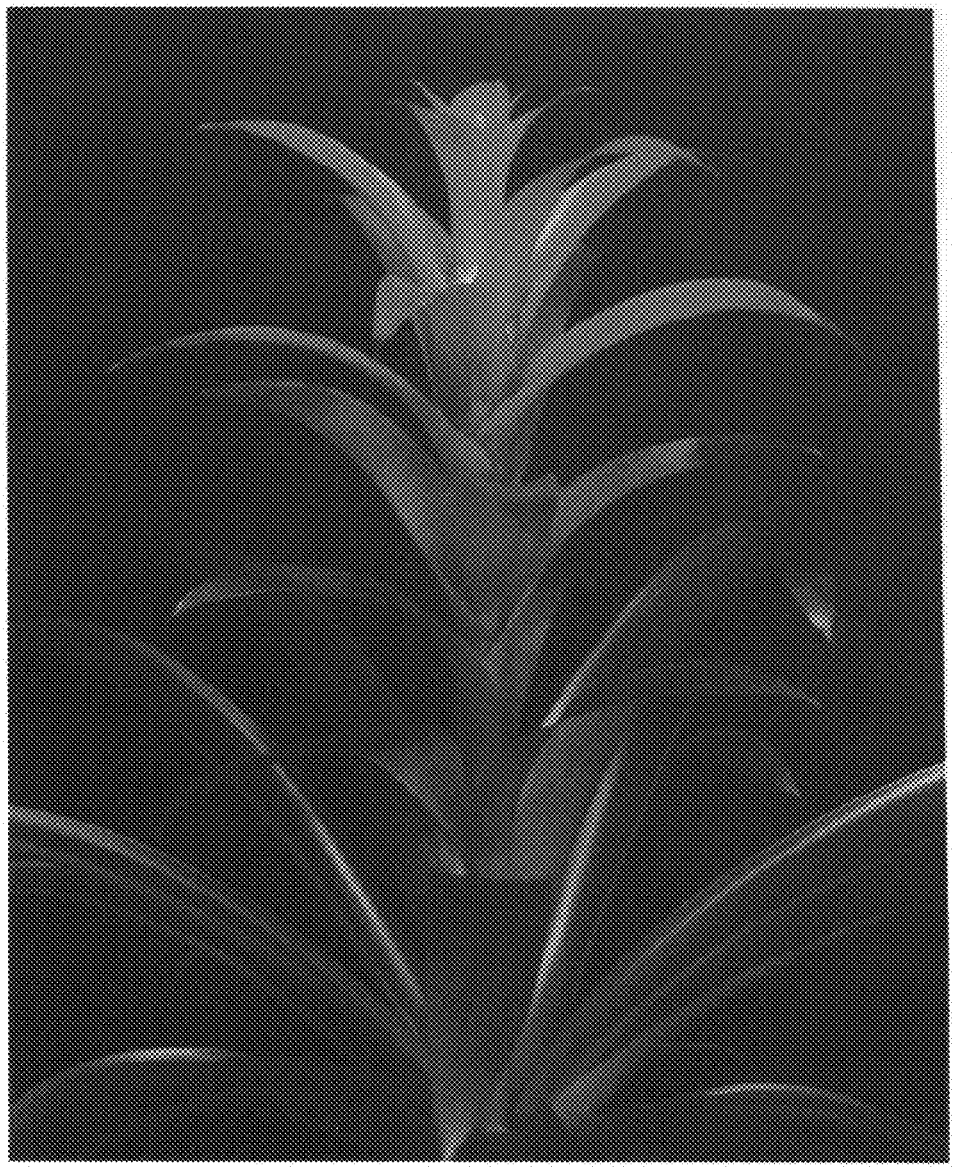
FIG. 2 shows a close-up top view perspective of the inflorescence and top bracts produced by a typical potted, flowering plant of 'JUNO', at 12 months of age from potting size.

'JUNO' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter, and number of leaves can result depending on the size of the plant at the time that flowering is induced. Since treatment to induce flowering disrupts normal watering and fertilization regimens, flowering treatment of relatively smaller plants adversely affects the growth of the plant.

The afore mentioned photographs, together with the following observations, measurements and values describe the new *Guzmania* 'JUNO' as grown in a greenhouse in Assendelft, The Netherlands, under conditions which closely approximate those generally used in commercial practice. Plants of 'JUNO' were grown in a greenhouse with day temperatures ranging from 20° C. to 28° C. and night temperatures ranging from 18° C. to 23° C. No artificial lighting or photoperiodic treatments were conducted, but plants of 'JUNO' are forced into flowering. The following fertilizer is added when growing plants of 'FREYA': 1 part nitrogen, 0.6 parts phosphor, 2 parts Kalium and 0.1 parts magnesium.

Color references are made to The Royal Horticultural Society Colour Chart (R.H.S.), 2001 edition, except where general colors of ordinary significance are used. Color values were taken under daylight conditions in a greenhouse in Assendelft, The Netherlands. The age of the plants of 'JUNO' described is about 17 weeks after flowering treatment.

Classification:

*Botanical.*—*Guzmania* sp.

Parentage: Naturally occurring whole plant mutation of *Guzmania* (hybrid) 'LUNA' (unpatented).

Plant:

*General appearance and form.*—Height: About 57 cm (when flowering). Width: About 70 cm. Shape: Funnel form rosette.

*Growth habit.*—Stemless.

*Plant vigor.*—Good.

*Flowering season.*—A fully grown plant can flower year round, starting 17 weeks after induction of natural light or through flowering treatment.

*Cold tolerance.*—Frost tender. Temperatures below 5° C. may damage plants.

*Fragrance.*—None.

Foliage:

*Quantity.*—About 18 (depending on the size or the plant).

*Size of leaf.*—Length: About 45 cm (when flowering). Width: About 3.0 to 3.5 cm.

*Overall shape.*—Linear-lanceolate.

*Apex shape.*—Acuminate.

*Base shape.*—Strap-like around central axis.

*Margin.*—Entire.

*Texture* (*both surfaces*).—Smooth.

*Orientation.*—Leaf blades arch continuously from base.

*Color.*—Leaf color can vary somewhat depending on growing conditions. Mature: Upper surface: Green, RHS 147A. Under surface: Green, RHS 137A. Immature: Upper surface: Green, RHS 147A. Under surface: Green, RHS 137A. Venation: None.

Inflorescence:

*Borne.*—Erect stalks.

*Shape.*—Compound.

*Size.*—Length (increases with maturity): About 17. Diameter: About 18 cm.

*Time of bloom.*—A fully grown plant can produce an inflorescence containing about 100 flowers (depending on the size of the plants), and can bloom the whole year starting about 17 weeks after natural induction or through flowering treatment.

*Duration of bloom.*—Each flower blooms one (1) day and the total blooming of the whole inflorescence is about five (5) weeks.

*Petals.*—Number: 3 per flower. Length: About 6.0 cm. Width: About 0.5 cm. Overall Shape: Ligulate. Apex Shape: Obtuse. Base Shape: Fused. Color: Upper and Under surfaces: Yellow, RHS 8C.

*Sepals.*—Number: 3 per flower. Length: About 3.5 cm. Width: About 0.5 cm. Overall Shape: Ligulate. Apex Shape: Acute. Base Shape: Fused. Color: Translucent.

Bracts:

*Scape bracts.*—Quantity: About 12. Arrangement: Alternate. Size: Length: About 27 cm(lowest) to about 18 cm (scape bracts positioned just below the primary bracts). Width: About 3.5 cm. Overall shape: Lanceolate. Apex shape: Acute. Base shape: Fused. Margin: Entire. Texture: Smooth. Color: Upper surface: Green, RHS 147A, with red-purple, RHS 61B. Scape bracts become more red-purple in color, closer to the primary bracts. Under surface: Green, RHS 137A, with red-purple, RHS 61B. Scape bracts become more red-purple in color, closer to the primary bracts.

*Primary bracts*.—Quantity: About 9. Arrangement: Alternate. Size: Length: About 17 cm (lowest) to about 9 cm (primary bracts become shorter closer to the top of plant). Width: About 3.0 cm. Overall shape: Lanceolate. Apex shape: Acute. Base shape: Fused. Margin: Entire. Texture: Smooth. Color: Upper and Under surfaces: pinkish-red, RHS 47A.

*Floral bracts*.—Disposed within the inflorescence.

Productive organs:

*Androecium*.—Stamen: Number: 6 per flower. Length: About 5.0 cm. Diameter: About 1.0 mm. Color: White, (too small to qualify RHS value). Anther: Length: About 0.6 cm. Color: Cream, (too small to qualify RHS value). Pollen: Amount: Scarce. Color: Cream (too small to qualify RHS value).

*Gynoecium*.—Pistil: Number: 1 per flower. Length: About 5.5 cm. Stigma: Shape: 3-parted. Width: About 4.0 mm. Color: White, (too small to qualify RHS value). Style: Length: About 4.5 cm. Color: White, (too small to qualify RHS value). Ovary: Position: Superior. Shape: Conical. Length: About 0.6 cm. Diameter: About 0.3 cm. Color: Light green, RHS 144C.

Seeds/fruit: Sterile hybrid, therefore, no seed or fruit produced.

Disease/pest resistance: No observations made.

Disease/pest susceptibility: No observations made.

We claim:

1. A new and distinct *Guzmania* plant named 'JUNO', substantially as illustrated and described herein.

* * * * *